United States Patent [19]

Gutbier

[11] Patent Number: Plant 7,250

[45] Date of Patent: Jun. 19, 1990

[54] POINSETTIA PLANT '21-85'

[75] Inventor: Gregor Gutbier, Linz a. Rhein, Fed. Rep. of Germany

[73] Assignee: Paul Ecke Ranch, Inc., Encinitas, Calif.

[21] Appl. No.: 266,533

[22] Filed: Nov. 3, 1988

[51] Int. Cl.[5] ..... A01H 5/00

[52] U.S. Cl. ..... Plt./86

[58] Field of Search ..... Plt./86

*Primary Examiner*—James R. Feyrer

*Attorney, Agent, or Firm*—Arnold, White & Durkee

[57] ABSTRACT

Described is a new Poinsettia cultivar, '21-85', that is a vigorous, self-branching Poinsettia of medium height with large white flower bracts. '21-85' has short bract petioles which cause the bracts to be tightly clustered around the cyathia. '21-85' can be flowered in a relatively cool greenhouse, making it economical to grow commercially. '21-85' is a sport of the cultivar described in U.S. Plant Pat. No. 5,492.

1 Drawing Sheet

BACKGROUND OF THE INVENTION

'21-85' is a vigorous, self-branching Poinsettia of medium height and large white flower bracts. The bract petioles are short causing the bracts to be tightly clustered around the cyathia. It has self-branching traits which make it desirable for branched plant production. '21-85' can be flowered in a relatively cool greenhouse, making it economical to grow commercially.

This new Poinsettia cultivar originated as a color sport of the red bracted cultivar described in U.S. Plant Pat. No. 5,492, in a greenhouse in Linz/Rhein, West Germany. This white sport has all the self-branching traits and other desirable growth characteristic of the cultivar of U.S. Plant Pat. No. 5,492. After selection, vegetatively reproduction of this plant by stem cuttings for test purposes in Linz/Rhein, West Germany, and clones of the plant were subjected to successive generations of vegetative propagation which demonstrated that its white bract coloration and other distinctive characteristics hold true from generation to generation.

DESCRIPTION OF THE PHOTOGRAPHS

'21-85' is illustrated in the accompanying color photographs. The upper photo is a side view of typical unbranched plant in full flower. The lower photo is a top view of a plant showing flower and bract formation.

DESCRIPTION OF THE PLANT

The following is a detailed description of this new Poinsettia as observed in Encinitas, Calif., during December, 1987. Observations were recorded from flowering plants, grown as 3 unpinched plants per pot. The pot was 14 cm. in diameter and 11 cm. in height. Color designations were compared to the 1986 edition of R.H.S. Colour Chart, first published in 1966 by the Royal Horticultural Society, London, England.

THE PLANT

Origin: Sport of the cultivar described in U.S. Plant Pat. No. 5,492.

Classification:

*Botanic.*—*Euphorbia pulcherrima* Willd.

*Common name.*—Poinsettia.

*Cultivar name.*—'21-85'.

Form: Shrub.

Height: Medium.

Growth habit: As a single stemmed plant, upright and vigorous. In full flower, the stem is terminated at a large inflorescence, with several smaller flowering side shoots lower on the stem. Observation of 3 plants in a pot with an overall height of 47 cm. and an overall width of 56 cm. were made. The bract diameter of individual flowers was 34–36 cm.

Branching: Branching can be enhanced by removal of the stem tip. Then, several flowering branches with equal vigor may develop on a single plant. The stem color is green, near RHS 137C.

Growth rate: Very fast. Rooting of stem cuttings occurs in 12–18 days under intermittent mist. The plant will flower in about ten weeks under continuous long night conditions and night temperatures of about 16–18 degrees C.

Foliage: The foliage is clean and uniformly green from bottom to top of the plant. The leaves are of medium size, leaf blades typically being about 13–15 cm. long and about 8–10 cm. wide with leaf petioles about 5–6 cm. long.

Leaf shape: Typical leaves are ovate with obtuse bases and acuminate tips. Leaf margins are mostly entire with some modest lobing and undulation.

Color:

*Upper side.*—Near RHS 137A.

*Under side.*—Between RHS 138A and RHS 138B.

Retention: The foliage retention is good even under low light intensities in the consumer's home.

Bracts: Generally there are 21–24 white bracts of various sizes subtending the cyathia. The primary bracts have blades typically 16–18 cm. long and 10–11 cm. wide with petioles about 2 cm. long.

Shape: Bracts are mostly ovate with acute bases and acuminate tips. Primary bracts are mostly entire; some with modest lobing on either side of the bract. The bract surface is only slightly rugose, but generally smoother than the parent plant, U.S. Plant Pat. No. 5,492.

Color:

*Upper side.*—White, between RHS 155A and RHS 1D.

*Under side.*—Near RHS 155A.

Vein coloration: The mid-vein and usually the lateral veins on the upper bract surface are overlaid with a thin green line, near RHS 137A, which are only superficially apparent and do not distract from the overall white appearance of the bracts. The color of the bract veins on the under surface is light yellow-green, near RHS 145C.

Cyathia: Generally, 18–21 cyathia (flowers) are present when the plant is in "full bloom". Each cyathium is about 7–8 mm long and about 6–7 mm wide, green in color and fading to yellow toward the distal end. Sometimes one, but more often two, bright yellow nectar cups protrude from the side of the cyathium. The flower pedicel is also green and about 6–7 mm in length. The anthers protruding from the cyathia are white. The morphology of the cyathia is like that of the parent, U.S. Plant Pat. No. 5,492. The color of the cyathia differs, however.

What is claimed:

1. A new and distinct Poinsettia cultivar, substantially as herein shown and described, distinguished by its large white flower bracts, and short bract petioles which cause the bracts to be tightly clustered around the cyathia.

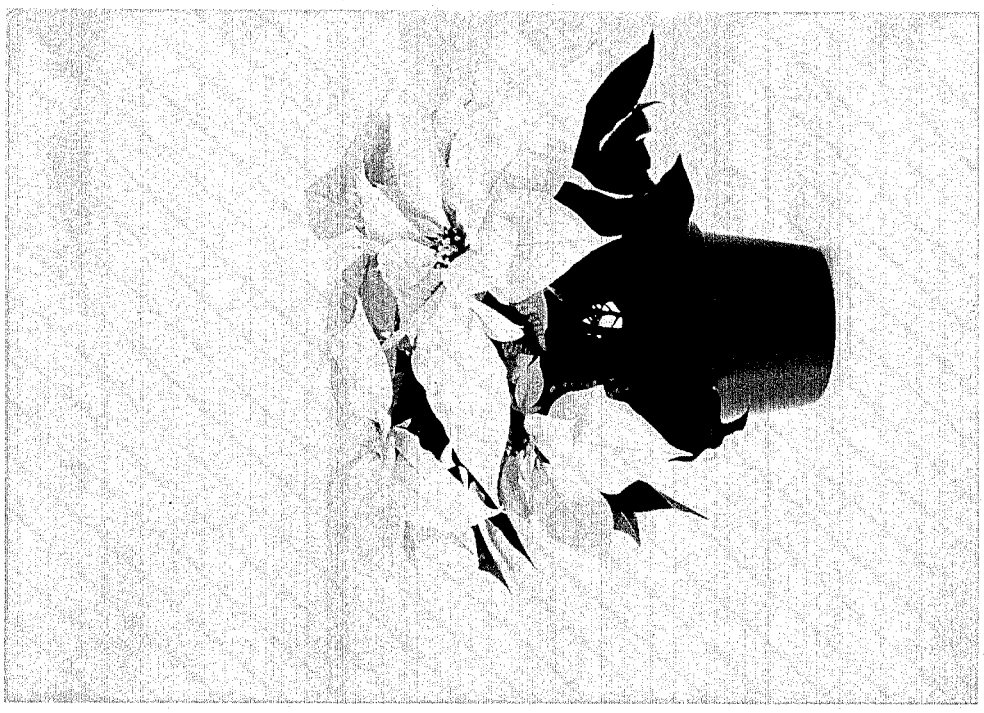
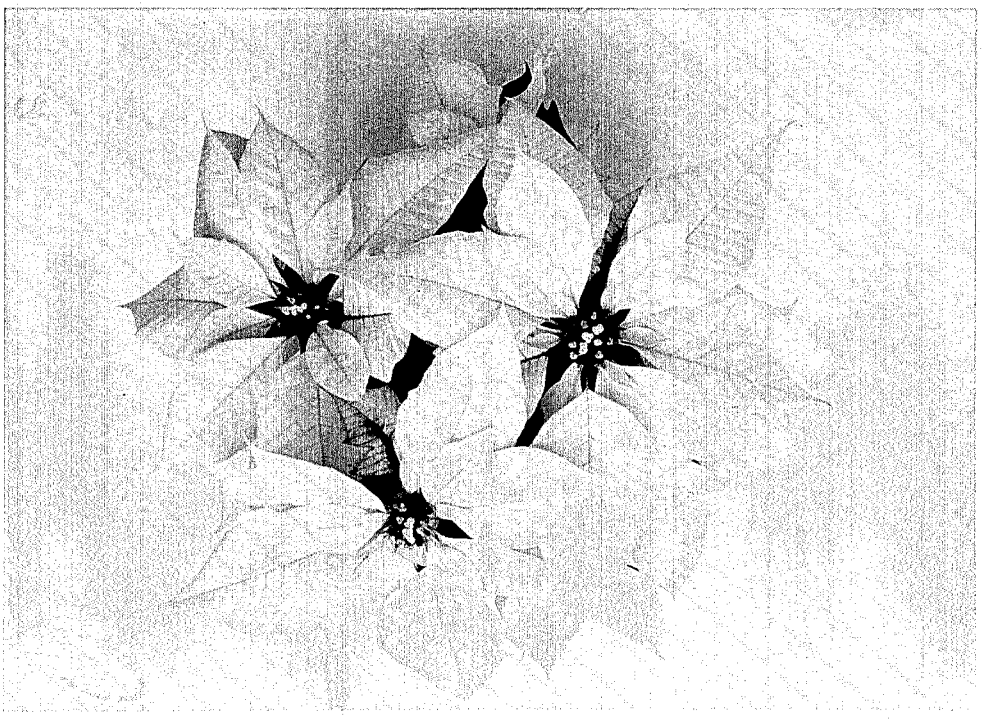

* * * * *